US006392114B1

United States Patent
Shields et al.

(10) Patent No.: US 6,392,114 B1
(45) Date of Patent: May 21, 2002

(54) SOLID CATALYST ALKYLATION PROCESS WITH REGENERATION SECTION AND HYDROGEN FRACTIONATION ZONE

(75) Inventors: Dale J. Shields, Buffalo Grove; Paul A. Sechrist, Des Plaines, both of IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 09/475,702

(22) Filed: Dec. 30, 1999

(51) Int. Cl.[7] .............................. C07C 2/60; C07C 2/58
(52) U.S. Cl. ........................ 585/719; 585/712; 585/713; 585/727
(58) Field of Search .................. 585/713, 712, 585/714, 727; 502/53

(56) References Cited

U.S. PATENT DOCUMENTS

| 4,083,800 A | * | 4/1978 | Herbstman et al. | .......... 252/415 |
| 5,310,713 A | | 5/1994 | Kojima et al. | ................. 502/30 |
| 5,489,732 A | | 2/1996 | Zhang et al. | ................ 585/467 |
| 5,672,798 A | | 9/1997 | Zhang et al. | ................ 585/467 |
| 5,675,048 A | | 10/1997 | Zhang et al. | ................ 585/467 |

OTHER PUBLICATIONS

Handbook of Petroleum Refining Processes, Second Edition, Ch. 1.4 and 1.5, edited by Robert A. Myers, McGraw–Hill, New York, 1997.*

* cited by examiner

Primary Examiner—Thuan D. Dang
(74) Attorney, Agent, or Firm—John G. Tolemei; John F. Spears, Jr,; Michael A. Moore

(57) ABSTRACT

An alkylating agent alkylates an alkylation substrate in a solid catalyst alkylation process in which an alkylation reactor produces a reaction effluent and a catalyst regeneration zone produces a hydrogen-containing regeneration effluent. The alkylation effluent passes to an alkylate fractionation zone, while the regeneration effluent passes to a hydrogen fractionation zone to remove hydrogen and produce a hydrogen-depleted stream that passes to the alkylate fractionation zone. The process recycles hydrogen, and can recycle halogen-containing species as well, within the process while preventing admixture of hydrogen with the alkylating agent. This invention is particularly applicable to alkylation processes that use an olefinic alkylating agent.

20 Claims, 2 Drawing Sheets

SOLID CATALYST ALKYLATION PROCESS WITH REGENERATION SECTION AND HYDROGEN FRACTIONATION ZONE

FIELD OF THE INVENTION

This invention relates to the alkylation of hydrocarbons to produce useful chemicals and motor fuel. This invention specifically relates to a process for producing motor fuel blending components by alkylating paraffins with olefins using a solid catalyst, which is regenerated in the presence of hydrogen.

BACKGROUND OF THE INVENTION

Hydrocarbon alkylation is widely used in the petroleum refining and petrochemical industries to produce a variety of useful acyclic and cyclic hydrocarbon products that are consumed in motor fuel, plastics, detergent precursors, and petrochemical feedstocks. Alkylation comprises reacting an alkylation substrate feedstock such as isobutane and benzene with an alkylation agent feedstock such as $C_2$–$C_{22}$ olefins. For example, large amounts of paraffins for high-octane gasoline are produced by the alkylation of isobutane with butenes. In addition, valuable aromatic hydrocarbons including cumene, ethylbenzene, and $C_{16}$–$C_{22}$ linear alkylaromatics are produced in large amounts by alkylating benzene with olefins of the appropriate carbon number. The variety of feedstock alkylation substrates and alkylation agents and the passage of time has led to the development of a number of effective alkylation technologies which are employed in large scale commercial facilities. Much of the installed base of alkylation capacity uses liquid phase hydrofluoric acid, generally referred to as HF, as the catalyst.

FIGS. 1.4.3 and 1.4.4 of the book entitled *Handbook of Petroleum Refining Processes*, edited by Robert A. Meyers, Second Edition, McGraw-Hill, New York, 1997, show process flow diagrams of HF alkylation processes, including the product recovery facilities for recovering the hydrocarbons in the alkylation reactor effluent. Referring to these figures, the hydrocarbon phase, which contains alkylate, isobutane, some propane, and dissolved HF, flows from the acid settler, is preheated, and passes to a fractionation column, which is commonly called an "isostripper." The hydrocarbon phase effluent from the reactor section enters at a feed tray near the top of the isostripper so that the isostripper consists mostly of a stripping section, except for a small rectification section on the top of the isostripper. The stripping section strips the more volatile HF, propane, and isobutane from the descending liquid alkylate, and product alkylate is recovered from the bottom of the isostripper. A bottom reboiler and one or more side reboilers add heat to the isostripper. When applicable, saturate field butane feed comprising isobutane and normal butane is fed to the stripping section of the isostripper at a tray below the reactor effluent feed tray, and any normal butane that may have entered the process is withdrawn from a sidedraw tray located below the field butane feed tray. Unreacted recycle isobutane is also withdrawn as a sidedraw, via a tray located between the reactor effluent and field butane feed trays. The rectification section reduces the concentration of the less volatile alkylate in the overhead vapor stream and thereby provides for efficient rejection of propane from the process. The overhead stream, which contains isobutane, propane, and HF, is condensed in an overhead condenser and collects in an overhead receiver. A drag stream of condensed overhead material undergoes further processing and separation in order to prevent an accumulation of propane in the process and to recycle isobutane and HF.

The use of HF in these motor fuel and detergent processes has a long record of highly dependable and safe operation. However, the potential damage from an unintentional release of any sizable quantity of HF and the need to safely dispose of some byproducts produced in the process has led to an increasing demand for alkylation process technology which does not employ liquid phase HF as the catalyst. U.S. Pat. No. 5,672,798, for example, discloses alkylating paraffinic hydrocarbons such as isobutane with olefinic hydrocarbons such as propylene or butenes in a fluidized riser-reactor using a solid catalyst. The effluent of the riser-reactor comprises the desired alkylate product, byproducts of the alkylation reaction, unreacted isobutane, and solid catalyst. The solid catalyst is separated and the remainder of the riser-reactor effluent passes to product recovery facilities.

Numerous solid alkylation catalysts have been described in the open literature. The previously cited U.S. Pat. No. 5,672,798 teaches a number of suitable solid catalysts that contain or have been treated with a Lewis acid, such as a large pore zeolite and a Lewis acid such as boron trifluoride and aluminum chloride, a large pore crystalline molecular sieve and a gaseous Lewis acid, a crystalline transition alumina treated with a Lewis acid, an acid washed silica treated with antimony pentafluroride, and a refractory inorganic oxide impregnated with a monovalent cation whose bound surface hydroxyl groups have been at least partially reacted with a Friedel-Crafts metal fluoride, chloride, or bromide.

These catalysts appear to suffer from slight but significant halogen loss rates when used at commercially useful alkylation reactor conditions. While some catalysts have a sufficiently useful halogen retention to allow the performance of alkylation, the gradual depletion of halogen results in a change in product composition and also requires the occasional replenishing of the halogen content of the catalyst. Some of the halogen loss is believed to be caused by the stripping of halogen from catalytically active sites of the catalyst by isobutane and also by the deposition on the catalytically active sites of heavy compounds. As used herein, the term "heavy compounds" means molecules that have at least one carbon atom more than the number of carbon atoms than the highest number of carbon atoms of those molecules that are desired to be in the alkylate.

However, in addition to exhibiting halogen loss, these catalysts also seem to suffer from unacceptably high deactivation rates when employed at commercially feasible conditions. While some catalysts have a sufficiently useful lifetime to allow the performance of alkylation, the rapid change in activity results in a change in product composition and requires the periodic regeneration of the catalyst. Such periodic regeneration is typically accomplished by removing deactivated catalyst from the reaction zone, reactivating the catalyst in a separate zone, and returning the reactivated catalyst to the reaction zone. Some of the deactivation is believed to be caused by the deposition of heavy compounds on the catalytically active sites of the catalyst.

Continuous processes for alkylation that are not subject to periodic reaction zone stoppages or variation in the product stream composition are desirable, and the previously mentioned U.S. Pat. No. 5,672,798 describes such a process. In order to remove the heavy hydrocarbon deposits and at least partially restore the activity of the catalyst, U.S. Pat. No. 5,672,798 teaches contacting the catalyst within the process with hydrogen in two separate and simultaneous modes of regeneration: a mild liquid-phase washing and a hot vapor-phase stripping.

The hot vapor-phase stripping which is disclosed in U.S. Pat. No. 5,672,798 consists of contacting the catalyst with a vapor-phase gas stream at a temperature that is typically greater than that employed in the alkylation zone. Because the gas stream uses hydrogen and the contacting occurs at an elevated temperature, hot vapor-phase stripping, which is also referred to in U.S. Pat. No. 5,672,798 as "hydrogen stripping" or "severe regeneration." U.S. Pat. No. 5,627,798 teaches that the presence of some isobutane in the gas stream is desirable to increase the heat capacity of the gas and thereby to increase the catalyst heat-up rates. This hot hydrogen-isobutane stripping removes liquid phase hydrocarbons and deposits of heavy compounds from the catalyst and produces a vapor phase regeneration zone effluent stream. U.S. Pat. No. 5,672,798 teaches that this regeneration zone effluent stream is preferably first cooled sufficiently to condense substantially all of the hydrocarbons within the stream and then subjected to vapor-liquid phase separation. The recovered liquids pass to the products recovery facilities, and the hydrogen is recycled to the severe regeneration zone.

The mild liquid-phase washing which is disclosed in U.S. Pat. Nos. 5,310,713 and 5,672,798 comprises contacting the catalyst with a liquid-phase stream which is preferably the feed alkylation substrate (e.g., isobutane). This contacting generally occurs at a lower temperature than that of severe regeneration, and partly for this reason this contacting is often referred to as "mild regeneration." U.S. Pat. Nos. 5,310,713 and 5,672,798 teach that hydrogen is preferably dissolved in this liquid-phase stream by a controlled addition up to the point of the stream containing the stoichiometrically required amount of hydrogen. These patents also teach that, for purposes of computing the stoichiometric requirement, the catalyst is analyzed in a laboratory for its heavy hydrocarbon deposit and the heavy hydrocarbon deposits are assumed to be composed of monoolefinic octenes. Some of this hydrogen is chemically consumed by saturating unsaturated hydrocarbons on the catalyst surface. In addition to reactivated catalyst, which is the desired product of the mild regeneration, a liquid-phase effluent is also recovered. This mild regeneration effluent usually contains hydrogen up to the point of saturation of hydrogen. The mild regeneration effluent combines with the riser-reactor effluent, and the combined effluents flow to the product recovery facilities.

The amount of hydrogen that is typically introduced into either the severe or mild regeneration zone is in excess of the amount that reacts with heavy hydrocarbon deposits in that zone, and therefore hydrogen is present in the severe regeneration effluent and/or the mild regeneration effluent. Because this hydrogen in these effluent(s) can still be useful in regenerating the catalyst, it is desirable to recycle this hydrogen to the regeneration zone(s). Therefore, methods are sought to recover and recycle hydrogen that is present in the regeneration effluent(s).

SUMMARY OF THE INVENTION

This invention is a paraffin-olefin alkylation process using a solid catalyst with a catalyst regeneration zone, in which an alkylation reactor effluent passes to an alkylate fractionation zone and a hydrogen-containing regeneration effluent passes to a hydrogen fractionation zone. While the alkylate fractionation zone recycles to the alkylation reactor compounds such as unreacted paraffinic feed or such as halogen-containing species to maintain the halogen content of the catalyst in the alkylation reactor, the hydrogen fractionation zone recycles molecular hydrogen to the regeneration zone to reactivate the catalyst. The hydrogen fractionation zone prevents molecular hydrogen from mixing with the reactor effluent, from entering the alkylate fractionation zone, and thus from being recycled to the alkylation reactor. By segregating molecular hydrogen in the regeneration effluent from the reactor effluent, the alkylate fractionation zone can in one embodiment of this invention produce a recycle stream comprising unreacted paraffinic feed or halogen-containing species that is substantially free of molecular hydrogen, that is, less than 500 wt-ppm molecular hydrogen. Therefore, the hydrogen fractionation zone maximizes the use of molecular hydrogen for regeneration and minimizes passing of molecular hydrogen to the alkylation reactor.

This invention is an improvement over prior art processes such as U.S. Pat. No. 5,672,798, which does not pass either the mild regeneration effluent or the severe regeneration effluent to a hydrogen fractionation zone, and therefore causes the olefin alkylating agent to be used very inefficiently. In the case of the mild regeneration effluent, U.S. Pat. No. 5,672,798 teaches combining the mild regeneration effluent with the riser-reactor effluent and passing the combined effluents to the product recovery facilities. Thus, the hydrogen chloride in the riser-reactor effluent inevitably becomes mixed with the molecular hydrogen in the regeneration effluent, and because the volatilities of molecular hydrogen and hydrogen chloride at commercially feasible fractionation conditions are relatively close so that molecular hydrogen and hydrogen chloride are difficult to separate from each other using the isostripper, the isostripper overhead stream contains both molecular hydrogen and hydrogen chloride. Therefore, recycling of the overhead stream to the inlet of the riser-reactor in order to replenish the chloride content of the catalyst would also recycle molecular hydrogen to the inlet of the riser-reactor. This has a detrimental effect on the alkylation performance, because molecular hydrogen is introduced at a point where unreacted olefin is present, which allows molecular hydrogen to saturate the olefin and thereby to render olefin ineffective as an alkylating agent. In contrast, by preventing molecular hydrogen from entering the alkylate fractionation zone, this invention recovers and recycles molecular hydrogen in the mild and/or severe regeneration effluents, without incurring the detrimental effect of loss of effective alkylating agent. In the case of the severe regeneration effluent, U.S. Pat. No. 5,672,798 teaches passing the severe regeneration effluent to a vapor-liquid separator, separating a heavy hydrocarbon liquid phase from the vapor phase, and passing the liquid phase to conventional product recovery facilities. It has now been recognized, however, that a significant portion of the molecular hydrogen that enters the vapor-liquid separator with the severe regeneration effluent exits the vapor-liquid separator with the liquid phase, rather than the vapor phase, because molecular hydrogen is dissolved in, entrained in, or otherwise contained in or carried with the liquid phase. Therefore, despite the use of a vapor-liquid separator, the process of U.S. Pat. No. 5,672,798 nevertheless passes significant and unacceptable quantities of molecular hydrogen to the isostripper and in turn to the riser-reactor.

Another advantage of this invention over the process in U.S. Pat. No. 5,672,798 is a reduction in the capital cost and operating costs of the isostripper. This invention not only prevents the mixture of molecular hydrogen and hydrogen chloride but also that of molecular hydrogen and the alkylation substrate (e.g., isobutane), in the isostripper. Isobutane is generally introduced in stoichiometric excess at alkylation conditions, is therefore usually present in the alkylation reaction effluent, and is accordingly recycled by the isostripper to the alkylation reaction zone. Any molecular hydrogen entering the isostripper would thus have to be separated not only from hydrogen chloride but also from the isobutane. However, this latter separation requires a significant increase in the number of trays, especially in the upper section of the isostripper, as well as a significant increase in the reboiler duty. By using a hydrogen fractionation zone, this invention avoids the costs associated with adding these additional trays and providing additional heat utilities.

Therefore, a broad objective of this invention is to alkylate paraffins with olefins using a solid catalyst that is regenerated in the presence of hydrogen. Another broad objective of this invention is to alkylate paraffins with olefins using a regenerable solid catalyst in which hydrogen is used efficiently for regeneration while avoiding any detrimental reaction of hydrogen and olefins. This invention is well-suited for processes that use a solid catalyst and in which halogen is used to maintain catalyst performance because this invention allows for recycling halogens in order to replenish the catalyst halogen content.

Accordingly, in a broad embodiment, this invention is an alkylation process comprising passing a first feed stream comprising a paraffinic alkylation substrate and a second feed stream comprising an olefinic alkylating agent to an alkylation reaction zone. The alkylation reaction zone is operated at alkylation conditions selected to react the paraffinic alkylation substrate and the olefinic alkylating agent in the presence of a solid catalyst to produce alkylate. The alkylation conditions are also sufficient to deposit heavy compounds on the solid catalyst in the alkylation reaction zone. An alkylation reaction effluent comprising the alkylate and the paraffinic alkylation substrate is withdrawn from the alkylation reaction zone. A first catalyst stream comprising solid catalyst having heavy compounds deposited thereon is withdrawn from the alkylation reaction zone. At least a portion of the first catalyst stream passes to a first regeneration zone. The solid catalyst having heavy compounds deposited thereon is contacted with molecular hydrogen in the first regeneration zone at first regeneration conditions selected to remove at least a portion of the heavy compounds from the solid catalyst having heavy compounds deposited thereon and to at least partially regenerate the solid catalyst having heavy compounds deposited thereon. A second catalyst stream comprising at least partially regenerated solid catalyst is withdrawn from the first regeneration zone. At least a portion of the second catalyst stream passes to the alkylation reaction zone. A first regeneration effluent comprising molecular hydrogen and the heavy compounds is withdrawn from the first regeneration zone. At least a portion of the first regeneration effluent passes to a hydrogen fractionation zone. A hydrogen-enriched stream having a first concentration of molecular hydrogen is recovered from the hydrogen fractionation zone. A hydrogen-depleted stream comprising the heavy compounds and having a second concentration of molecular hydrogen that is less than the first concentration of molecular hydrogen is also recovered from the hydrogen fractionation zone. At least a portion of the hydrogen-enriched stream passes to the first regeneration zone. At least a portion of the alkylation reaction effluent and at least a portion of the hydrogen-depleted stream passes to an alkylate fractionation zone. A recycle stream comprising the paraffinic alkylation substrate is withdrawn from the alkylate fractionation zone. The first feed stream is formed from at least a portion of the recycle stream. The alkylate is recovered from the alkylate fractionation zone.

INFORMATION DISCLOSURE

Chapters 1.4 and 1.5 of the book entitled *Handbook of Petroleum Refining Processes*, edited by Robert A. Meyers, Second Edition, McGraw-Hill, New York, 1997 describe HF alkylation processes for motor fuel production and detergent manufacture.

U.S. Pat. No. 5,489,732 (Zhang et al.); U.S. Pat. No. 5,672,798 (Zhang et al.); and U.S. Pat. No. 5,675,048 (Zhang et al.) disclose alkylation processes that use a solid catalyst which is regenerated by a "mild," low-temperature, liquid phase washing and by a "severe," hot vapor phase hydrogen stripping operation. The teachings of U.S. Pat. Nos. 5,489,732; 5,672,798; and 5,675,048 are incorporated herein by reference.

U.S. Pat. No. 5,310,713 (Kojima et al.) discloses a solid catalyst alkylation process wherein the reaction mixture is a liquid phase, the catalyst is treated with hydrogen, and the hydrogen treatment may be effected with either liquid-free catalysts or in the presence of liquid isobutane and a chloride source. The teachings of U.S. Pat. No. 5,310,713 are incorporated herein by reference.

DETAILED DESCRIPTION OF THE INVENTION

Figure 1:
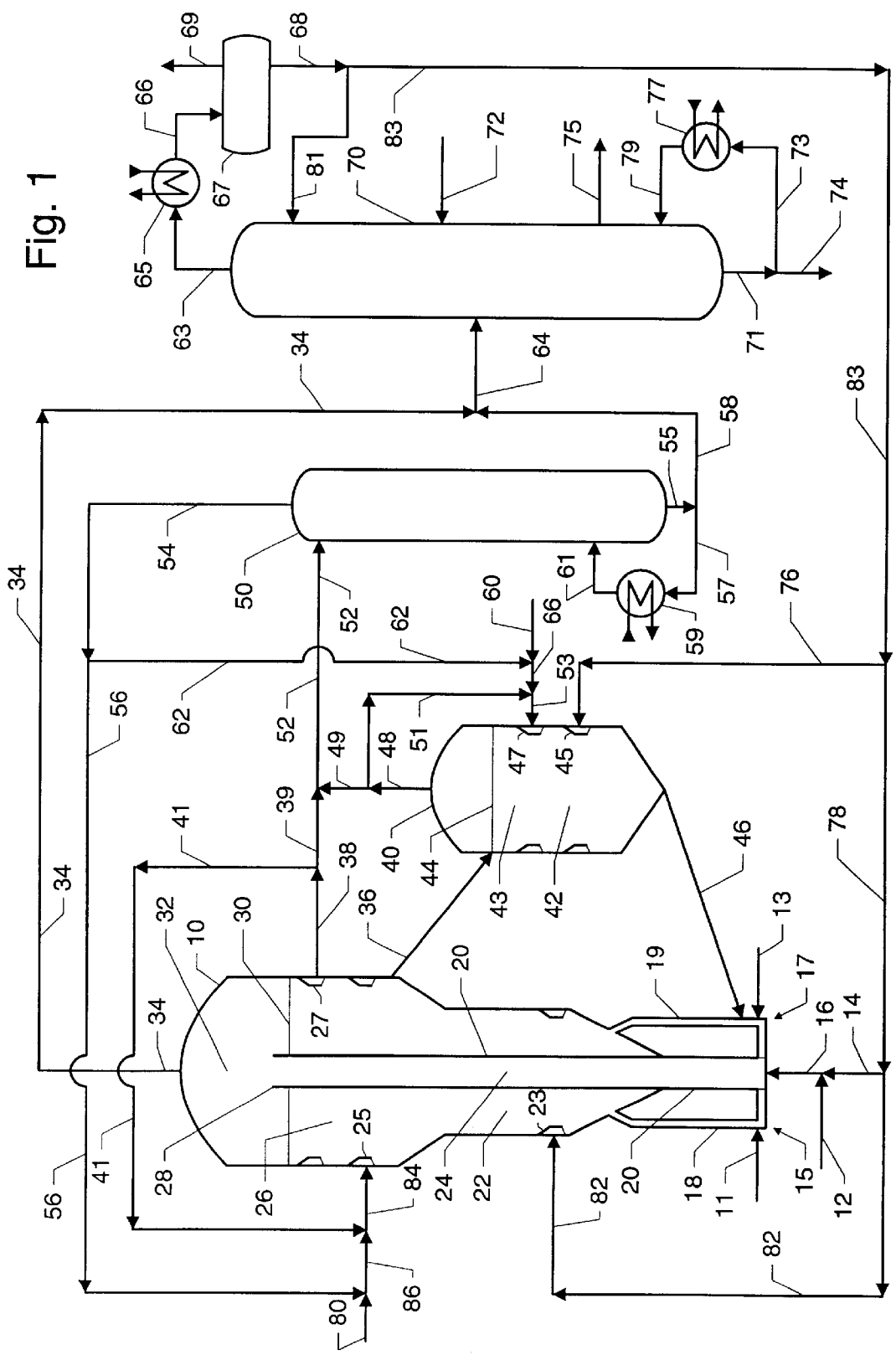
FIGS. 1–2 show process flow diagrams of two embodiments of the invention.

The feedstocks for this invention are an alkylation substrate and an alkylating agent. The alkylation substrate may be essentially any hydrocarbon which is retained as an easily flowable liquid phase material and which may be alkylated via solid catalyst at the conditions employed in the alkylation reactor. The alkylation substrate may be an aromatic hydrocarbon, if the objective is to produce such chemicals as ethylbenzene and cumene or to produce linear alkyl benzenes, which are sulfonated to detergents. Although benzene is the principal aromatic of interest, aromatics such as alkyl-substituted benzenes, condensed ring systems generally, and alkylated derivatives thereof may be used. Examples of such aromatics are toluene, ethylbenzene, propylbenzene, and so forth; xylene, mesitylene, methylethylbenzene, and so on; naphthalene, anthracene, phenanthrene, methylnaphthalene, dimethylnaphthalene, and tetralin. More than one aromatic can be used. If, on the other hand, the objective is to produce motor fuels, then the alkylation substrate may be a paraffinic hydrocarbon, such as a branched paraffin having from 4 to 6 carbon atoms. Suitable paraffinic hydrocarbons are illustrated by 2-methylpropane (commonly called isobutane), 2-methylbutane (or isopentane), 2,3-dimethylbutane, 2-methylpentane, and 3-methylpentane.

The alkylation substrate is alkylated with an alkylating agent. If the objective is to produce chemicals such as ethylbenzene or cumene or to produce motor fuels, then the alkylating agent is typically an olefinic hydrocarbon containing from 2 to about 6 carbon atoms. Examples of such olefins include ethylene, propylene, 1-butene, cis-2-butene, trans-2-butene, and iso-butene. However, if the objective is to produce linear alkyl benzenes, then the alkylating agent can be an olefinic hydrocarbon having from about 2 to about 20 carbon atoms, and usually from about 10 to about 15 carbon atoms. More than one olefin may be used. The alkylating agent may be chosen also from a variety of compounds other than olefins including monohydric alcohols. Suitable alcohols include ethanol and methanol. For instance, methanol is widely described in the literature as being useful in the methylation of benzene and toluene.

The subject process can be performed using any solid, that is, heterogeneous, catalyst which is stable and has the required activity and selectivity for the desired reaction at the conditions needed to maintain liquid phase reactants in the alkylation reactor. In addition, the catalyst must be capable of catalytically alkylating the alkylation substrate with the alkylating agent while also producing a reactor effluent stream that contains not only alkylate but also a hereinafter-described halogen-containing species. Types of catalysts that fulfill this requirement include catalysts that comprise a halide and catalysts that are catalytically promoted by a halide. Individual catalysts within these types are, however, not necessarily equivalent in terms of their catalytic ability to alkylate a given alkylation substrate with a given alkylating agent.

The present invention is applicable to a variety of hydrocarbon alkylation processes. However, the most widely practiced hydrocarbon alkylation process to which the present invention is applicable is motor fuel alkylation. Therefore, the discussion of the invention contained herein will be in reference to its application to a catalytic motor fuel alkylation system. It is not intended that such discussion limit the scope of the invention as set forth in the claims.

A large number of catalysts have been proposed for the production of motor fuel by alkylation including nonzeolitic catalysts and various zeolitic catalysts. Suitable nonzeolitic catalysts include sulfated zirconia and tungstated zirconia. Among suitable zeolitic catalysts, U.S. Pat. No. 4,384,161, for example, describes the use of a large pore zeolite and a Lewis acid. The zeolites referred to include ZSM-4, ZSM-3, the faujasites including zeolite Y, and mordenite. The Lewis acids mentioned in this reference include boron trifluoride and aluminum chloride. A somewhat similar catalyst system comprising a large pore crystalline molecular sieve such as a pillared silicate or an aluminophosphate or silicoaluminophosphate together with a gaseous Lewis acid is disclosed in U.S. Pat. No. 4,935,577. U.S. Pat. No. 5,157,200 describes a catalyst comprising a crystalline transition alumina, preferably eta or gamma alumina, which has been treated with a Lewis acid under anhydrous conditions. U.S. Pat. No. 5,157,196 describes a slurried solid catalyst, with the preferred catalyst being an acid washed silica, which has been treated with antimony pentafluoride. Both of these last two references describe a number of prior art heterogeneous paraffin alkylation catalysts.

A preferred paraffin alkylation catalyst comprises a refractory inorganic oxide impregnated with a monovalent cation, especially an alkali metal cation or an alkaline earth metal cation, and whose bound surface hydroxyl groups have been at least partially reacted with a Friedel-Crafts metal halide. Analogs of these catalysts without the metal cations are described in U.S. Pat. Nos. 2,999,074 and 3,318,820, which describe preparation techniques that can be applied to the preferred catalysts. The preferred refractory oxide is alumina having a surface area greater than 50 $m^2/g$, but the use of other oxides including titania, zirconia, silica, boria, and aluminum phosphate is contemplated. The preferred catalyst also contains a metal component active for olefin hydrogenation deposited on the inorganic oxide prior to reaction of the bound surface hydroxyl groups with the metal halides. This metal may be chosen from the group consisting of nickel, platinum, palladium, and ruthenium with the first three of these metals being preferred. The catalyst contains one or more monovalent metal or alkaline earth metal cations selected from the group consisting of lithium, sodium, potassium, cesium, silver, copper, beryllium, magnesium, calcium, and barium. After the deposition of these metals and the controlled calcination of the composite, the composite is reacted with a Friedel-Crafts metal halide. The metal may be aluminum, zirconium, tin, tantalum, gallium, antimony, or boron. Suitable halides are the fluorides, chlorides, and bromides.

Silicalites have been described as useful alkylation catalysts for the production of monoalkylbenzenes in U.S. Pat. No. 4,489,214 (J. R. Butler et al.) and as useful in methylating toluene to produce paraxylene in U.S. Pat. No. 4,444,989 (F. E. Herkes). The use of ZSM-5 zeolites in aromatic alkylation is described in U.S. Pat. No. 3,751,506. ZSM-5 zeolites that have been treated with one or more compounds or elements to improve their selectivity for paraselective alkylation of aromatic hydrocarbons are described in U.S. Pat. No. 4,420,418. The use of zeolite L, zeolite omega, and zeolite beta as alkylation catalysts for the selective alkylation of benzene is described in U.S. Pat. No. 4,301,316. The use of a number of natural and synthetic zeolites including clinoptilolite and zeolite Y as alkylation catalysts is described in U.S. Pat. No. 3,251,897.

The catalyst may be in the form of any suitable shape and size that results in a solid catalyst which flows readily in both dry and wet states and which is readily fluidized at the moderate liquid flow rates employed in a transport reactor such as a riser-reactor. The catalyst can therefore be present as small irregular particles or as uniformly shaped particles. It is preferred that the catalyst is present as "microspheres" having an average diameter of from about 0.1 to about 2.0 mm and more preferably less than about 1.0 mm.

The catalyst is generally employed in a transport reactor. Transport reactors are commonly used in hydrocarbon processing. In a transport reactor, the catalyst bed as a whole moves. Thus, a transport reactor can be contrasted with a fixed bed catalytic reactor and with an ebulliated bed catalytic reactor. In a fixed bed reactor the catalyst particles do not move, and in an ebullated bed reactor the catalyst particles are suspended in a fluid but the settling velocity of the catalyst particles balances the fluid upflow velocity so that the catalyst bed as a whole does not move. Although it is generally the case that the direction of catalyst flow through a transport reactor is upward, the direction may also be downward, horizontal, a direction that is intermediate between vertical and horizontal, or a combination of these directions.

When the direction of catalyst flow through a transport reactor is upward, the transport reactor is often called a riser-reactor. Riser-reactors are commonly used in hydrocarbon processing, such as fluidized catalytic cracking and more recently in fluidized solid bed motor fuel alkylation. In a common arrangement, a fluid hydrocarbon reactant engages a solid hydrocarbon conversion catalyst at the bottom of a riser-reactor and transports the catalyst in a fluidized state up the riser-reactor. During the ascent through the riser-reactor, the catalyst promotes certain desired conversion reactions among the reactants in order to produce desired products. A stream of catalyst and hydrocarbon products, by-products, and unreacted reactants if any discharges from the top of the riser-reactor into a separation zone. The hydrocarbons and the catalyst disengage in the separation zone, with the hydrocarbons being withdrawn overhead for recovery and the catalyst dropping by gravity to the bottom of the separation zone. Despite some deactivation that may have occurred to the catalyst in the riser-reactor, some of the catalyst that collects at the bottom of the separation zone usually has enough residual activity that it can be reused in the riser-reactor without first being withdrawn from the separation zone for regeneration. Such still-active catalyst is recirculated through a recirculation conduit from the bottom of the separation zone to the bottom of the riser-reactor, where the catalyst contacts reactants again.

Several methods are used for controlling the introduction of reactants and for controlling the recirculation of catalyst to the bottom of the riser-reactor. For example, one method is shown in a motor fuel alkylation process in U.S. Pat. No. 5,489,732 (Zhang et al.). Isoparaffins and olefins are introduced into the bottom of the riser-reactor, and the flow of catalyst through a single recirculation conduit to the bottom of the riser-reactor is controlled by several means including slide valves, other types of valves, lock hoppers, fluid flow control (reverse flow of liquid), screw conveyors, and L-valves. This patent also teaches that one reactant, isobutane, can also be introduced into the recirculation conduit for flushing by-product hydrogen from the recirculating catalyst.

Suitable operating conditions for the riser-reactor include a temperature of from about −50 to about 100° C. (−58 to 212° F.), preferably from about 0 to about 40° C. (32 to 104° F.), and a pressure as required to maintain the hydrocarbons present as a liquid. A moderate pressure in the general range of from about 1380 to about 4830 kPa(g) (200 to 700 psi(g)) is preferred with from about 3100 to about 4140 kPa(g) (450 to 600 psi(g)) being highly preferred. The weight ratio of catalyst per olefin in the riser-reactor is generally from about 3 to about 10. The liquid residence time in the riser-reactor is in the general range of from about 60 to about 150 seconds, and the catalyst residence time is in the general range of from about 90 to about 300 seconds. The riser-reactor is preferably designed and operated in a manner intended to promote plug flow (minimal backmixing) of the reactants, products, and catalyst within the riser-reactor. However, the liquid must flow upward faster than the catalyst in order to transport it.

It is generally preferred that the riser-reactor is operated with an excess of the substrate hydrocarbon compared to the alkylating agent. That is, it is preferred to operate with a ratio of the substrate paraffinic or aromatic hydrocarbon to an alkylating agent olefin at the reactor or tube entrance greater than 1:1, and preferably from about 5:1 to about 20:1 or higher as measured by the flow rates into the riser-reactor. It is highly preferred to operate with an abundance of isoparaffin compared to alkylating agent in a motor fuel alkylation process. Specifically, it is preferred that the molar ratio of isoparaffin to olefin being charged to the riser-reactor is greater than 2:1 and more preferably greater than 8:1. Ratios of 10:1 or higher can be employed for motor fuel alkylation, but ratios of about 100:1 or higher are generally considered to be uneconomical. Injection of the olefin at a number of points along the flow path of the hydrocarbon through the riser-reactor may be employed to maintain a higher average paraffin to olefin ratio, and preferably three injection points, in addition to the olefin injection at the bottom of the riser-reactor, are used. So, there are generally four or more olefin injection points along the length of the riser-reactor.

Provisions may be made to remove used catalyst from the process and to replace the used catalyst with fresh catalyst. Conventional-valved lock hopper systems may be used for this purpose.

The alkylation reaction effluent generally also contains the desired product of alkylation (alkylate), byproducts of side reactions, and unreacted feedstock. For example, in a process for the production of motor fuel by alkylating butenes with isobutane, alkylation reaction effluent typically comprises hydrocarbons having from 1 to 12 carbon atoms, including methane, ethane, propane, propene, butanes, butenes, pentanes, pentenes, hexanes, heptanes, octanes, nonanes, decanes, undecanes, and dodecanes. The alkylation reaction effluent generally comprises a halogen-containing species also, and the halogen-containing species is present in a concentration of generally greater than about 250 wt-ppm halogen, and usually from about 1000 to about 10000 wt-ppm halogen, based on the weight of the alkylation reaction effluent.

The halogen-containing species in the alkylation reaction effluent can be any halogen-containing species that is not readily separable from molecular hydrogen by fractionation. By not being readily separable from molecular hydrogen by fractionation, it is meant that the volatility difference between molecular hydrogen and the halogen-containing species is so small that, at the column operating pressure, either an undesirably low temperature (i.e., less than 32° F. (0° C.) would be required to produce reflux, or an undesirably high temperature (i.e., more than 500° F. (260° C.) would be required to produce boil-up, or a very large number of stages of fractionation (i.e., more than 20 theoretical stages) would be required to achieve the desired separation between molecular hydrogen and the halogen-containing species. Examples of halogen-containing species include molecular fluorine, molecular chlorine, molecular bromine, hydrogen fluoride, hydrogen chloride, and hydrogen bromide.

The catalyst that is employed in the alkylation reaction zone is withdrawn and subject to a mild regeneration, a severe regeneration, or both. When the withdrawn catalyst is subjected to both a mild and a severe regeneration, the mild and severe regeneration zones may be in parallel, so that one portion of the catalyst undergoes mild regeneration, another portion of the catalyst undergoes severe regeneration, and after having each been regenerated the two portions are returned to the alkylation reaction zone. Alternatively, the mild and severe regeneration zones may be in series, so that the portion of the catalyst that undergoes mild regeneration thereafter undergoes severe regeneration.

Mild regeneration comprises contacting the catalyst in a regeneration zone with a liquid-phase hydrocarbon, which is preferably the feed alkylation substrate, such as isobutane. Molecular hydrogen is dissolved in this liquid-phase stream up to the point of saturation of the molecular hydrogen in the liquid phase. Some of this molecular hydrogen is chemically consumed by saturating unsaturated hydrocarbons on the catalyst surface. The average residence time of catalyst particles in the liquid-phase hydrocarbon regeneration zone is preferably from about 2 to 20 minutes. Although the liquid-phase or mild regeneration zone may be performed in a separate vessel or conduit that is in communication with the reaction zone, preferably the mild regeneration occurs in the same vessel that contains the reaction zone, provided that the mild regeneration zone is separated from the reaction zone by suitable partitions or baffles. The temperature and pressure conditions in this regeneration zone are similar to those at the reaction zone outlet. The catalyst is treated with molecular hydrogen at a partial pressure between about 1 and about 2000 psi(g) (6.89 to 13790 kPa(g)). The temperature at which the catalyst is treated with molecular hydrogen varies between about 50 and about 572° F. (10 to 300° C.). Regeneration time depends inversely with temperature. Consequently, higher temps are favored if a shorter regeneration time is desirable, and for this reason temperatures even higher than 572° F. (300° C.) may be used, although these are not generally recommended. However, other factors favor low temperature regeneration. Regeneration at alkylation process conditions is most desirable in order to eliminate the costs of heating and cooling, and to make regeneration operationally simpler and easier. While regeneration may be done in the temperature range between about 50 and about 392° F. (10 to 200° C.), the temperature range of from about 100 to about 150° F. (38 to 66° C.) is preferred. A regeneration time on the order of about 20 minutes suffices to effect restoration of catalyst activity.

The mild regeneration effluent typically comprises molecular hydrogen and hydrocarbon that are introduced into the mild regeneration zone to effect mild regeneration. In a motor fuel alkylation process, the introduced hydrocarbon is typically isobutane. The mild regeneration effluent generally contains more than 0.5 mol-% hydrogen, but since the mild regeneration also generally employs an introduced hydrocarbon, the mild regeneration effluent will usually contain not more than 10 mol-% hydrogen, and commonly not more than 5 mol-% hydrogen. The concentration in the mild regeneration effluent of the hydrocarbon introduced to effect mild regeneration, which is usually the alkylation substrate (e.g., isobutane), will generally be from about 60 mol-% to about 90 mol-%. The balance of the regeneration effluent comprises compounds that are removed from the catalyst during mild regeneration. These compounds can comprise any of the hydrocarbons that are present in the alkylation reaction zone, including the alkylation substrate and the product alkylate, and heavy compounds, and the concentration of each of these compounds relative to each other in the mild regeneration effluent is approximately the same as that in the alkylation reaction effluent. The concentration in the mild regeneration effluent of alkylate product is generally less than 5 mol-%, and that of heavy compounds is generally less than 1 mol-%.

Severe regeneration comprises contacting the catalyst either with a vapor-phase gas stream at a relatively high temperature or with a liquid-phase or mixed liquid-vapor phase at a relatively low temperature. The zone in which this severe regeneration step is performed is operated in a manner that provides a longer residence time for the catalyst particles than that provided by the mild regeneration step. The average residence time of a catalyst particle should be at least 30 minutes and can reach about 12 to 24 hours. When regenerating with a vapor-phase gas stream, such as a vapor-phase hydrogen-rich gas stream, the temperature is in the range of generally from about 176 to about 932° F. (80 to 500° C.), and preferably from 212 to 482° F. (100 to 250° C.). The presence of some isobutane in this gas stream is desirable to increase the heat capacity of the gas and therefore increase catalyst heat up rates. The longer residence time that is required for this regeneration step allows the high temperature gas that is charged to the regeneration zone to vaporize liquid that flows into the severe regeneration zone.

The severe regeneration effluent typically comprises molecular hydrogen and hydrocarbon, if any, introduced into the severe regeneration zone to effect severe regeneration. In a motor fuel alkylation process, the introduced hydrocarbon is typically the alkylation substrate, which is usually isobutane. While the severe regeneration effluent generally contains greater than 0.5 mol-% hydrogen, the upper limit on the concentration of molecular hydrogen in the severe regeneration effluent depends on whether a hydrocarbon is introduced with molecular hydrogen in order to perform the severe regeneration. When molecular hydrogen is introduced without also introducing hydrocarbon for severe regeneration, the severe regeneration effluent will generally contain more than 80 mol-%, and commonly more than 90 mol-%, hydrogen. In this case, the balance of the regeneration effluent comprises compounds that are removed from the catalyst during severe regeneration. These compounds can comprise any of the hydrocarbons that are present in the alkylation reaction zone, including the alkylation substrate and the product alkylate, and heavy compounds, and the concentration of each of these compounds relative to each other in the severe regeneration effluent is approximately the same as that in the alkylation reaction effluent. The concentration in the severe regeneration effluent of alkylation substrate (e.g., isobutane) relative to that of alkylate product or to that of heavy compounds may be increased by flushing the catalyst with alkylation substrate prior to severe regeneration. Accordingly, the severe alkylation effluent generally contains the alkylation substrate, either because excess alkylation substrate is present on the catalyst when the catalyst was withdrawn from the alkylation reaction zone, or because alkylation substrate was used to flush the catalyst prior to severe regeneration. The concentration in the severe regeneration effluent of alkylate product is generally less than 5 mol-%, and that of heavy compounds is generally less than 1 mol-%.

When a hydrocarbon is introduced along with molecular hydrogen in order to perform severe regeneration, the severe regeneration effluent will generally contain less than 10 mol-% hydrogen, and commonly less than 5 mol-% hydrogen. In this case, severe regeneration occurs in a liquid or mixed liquid-vapor phase and the temperature is in the range of from about 150 to about 300° F. (66 to 149° C.). In this case also, the concentration in the severe regeneration effluent of the hydrocarbon used during severe regeneration, which is usually the alkylation substrate (e.g., isobutane), will generally be from about 70 mol-% to about 90 mol-%. As in the case of severe regeneration where molecular hydrogen is introduced without also introducing hydrocarbon, when hydrocarbon is introduced along with molecular hydrogen the concentration in the severe regeneration effluent of alkylate product is generally less than 5 mol-%, and that of heavy compounds is generally less than 1 mol-%.

In either mild or severe regeneration, the substrate-containing stream, if any, that is used is usually a distillate cut from a fractionation column and consequently contains other light paraffins besides isobutane. Thus, the mild or severe regeneration effluents may contain other hydrocarbons besides isobutane, such as methane, ethane, propane, normal butane, and pentanes. However, even when these other light hydrocarbons are present, the total concentration of these other light hydrocarbons in the mild or severe regeneration effluent is generally less than 25 mol-% of the concentration of the isobutane.

All of the catalyst passing from the alkylation reactor separation zone to the return to the alkylation reaction zone is preferably subject to one of the two forms of regeneration. A much smaller quantity of catalyst flows through the severe regeneration zone compared to the flow through the mild regeneration zone. The flow through the severe regeneration zone will be only between about 0.2 and about 20 weight percent, and preferably between about 0.4 and 5 weight percent, of the total catalyst flow that returns to the alkylation reaction zone.

The mild regeneration effluent, the severe regeneration effluent, or both, passes to the hydrogen fractionation zone. The hydrogen fractionation zone removes and recycles molecular hydrogen in the regeneration effluent of a solid catalyst alkylation process, thereby avoiding passing the molecular hydrogen to the alkylation reactor.

The hydrogen fractionation zone may comprise a rectification section, a stripping section, or both. Where the hydrogen fractionation zone comprises only a rectification section the hydrogen fractionation zone is referred to herein as a hydrogen rectifier, and where the hydrogen fractionation zone comprises only a stripping section the hydrogen fractionation section is referred to herein as a hydrogen stripper. Preferably, the hydrogen fractionation zone is a hydrogen stripper. The hydrogen fractionation zone contains generally from 5 to 50, and preferably from 10 to 20, trays. These numbers of trays are computed based on the assumption that each tray has an efficiency of 30%. If any of the actual trays has an efficiency greater than that assumed, then the numbers of required trays may be lower, and similarly if any of the actual trays has an efficiency that is less than that assumed, then the numbers of required trays may be higher. The hydrogen fractionation zone, including its trays and other internals, may be constructed from carbon steel.

In the case where the hydrogen fractionation zone is a hydrogen stripper, the operating conditions of the hydrogen stripper include a bottoms temperature of generally from about 200° F. to about 280° F. (93 to 138° C.) and preferably from about 230° F. to about 250° F. (110 to 121° C.), an overhead temperature of generally from about 150° F. to about 250° F. (66 to 121° C.) and preferably from about 180° F. to about 220° F. (82 to 104° C.), and an overhead pressure of generally from about 400 psi(g) to about 450 psi(g) (2758 to 3103 kPa(g)). The overhead stream of the hydrogen fractionation zone contains generally from about 10 to about 60 mol-% hydrogen. Generally greater than about 60%, preferably greater than about 90%, and more preferably greater than about 95% of the moles of molecular hydrogen that enter the hydrogen fractionation zone exit in the overhead stream. While removing molecular hydrogen from the regeneration effluent, the hydrogen fractionation zone should not strip too large of an amount of heavy compounds into the hydrogen fractionation zone overhead stream. Accordingly, the overhead stream of the hydrogen fractionation zone contains generally less than about 0.1 mol-%, and preferably less than about 0.01 mol-%, heavy compounds.

The hydrogen fractionation zone should ensure that molecular hydrogen is removed so that the bottom stream of the hydrogen fractionation zone has a concentration of molecular hydrogen of generally less than about 1.0 mol-% hydrogen, and preferably less than about 0.1 mol-% hydrogen. The remainder of the hydrogen fractionation zone bottom stream comprises liquid hydrocarbons, such as alkylate product and heavy compounds. The quantity of molecular hydrogen that is present in the bottom stream is such that, if all of the molecular hydrogen in the bottom stream ultimately passed to the alkylation reaction zone, then, even if all of that molecular hydrogen reacted with alkylating agent that is being charged to the alkylation reaction zone, then preferably less than 1%, and more preferably less than 0.5%, of the total alkylating agent charged to the alkylation reaction zone would be rendered ineffective by such reaction. An example of rendering the alkylating agent ineffective to react with the alkylation substrate is converting an olefinic alkylating agent feedstock to a paraffinic compound by reacting molecular hydrogen with carbon-carbon double bonds of the olefinic alkylating agent to form carbon-carbon single bonds. The alkylating agent is rendered ineffective to react with the alkylation substrate when the result of the reaction with molecular hydrogen produces a compound which does not have a carbon-carbon double bond. In another embodiment, the ratio of the moles of molecular hydrogen in the net bottom stream withdrawn from the hydrogen stripper to the moles of monoolefinic alkylating agent passed to the alkylation reaction zone is generally less than 0.01, and preferably less than 0.005 In yet another embodiment, the moles of molecular hydrogen in the net hydrogen stripper bottom stream is generally less than 1%, and preferably less than 0.5%, of the moles of carbon-carbon double bonds in the olefinic alkylating agent passed to the alkylation reaction zone.

In addition to removing molecular hydrogen from the regeneration effluent, the hydrogen fractionation zone may also remove hydrogen halide from the regeneration effluent. Removal of hydrogen halide is not, of course, a necessary function of the hydrogen fractionation zone, and thus hydrogen halide in the regeneration effluent may exit the hydrogen fractionation zone either via the overhead stream or via the bottom stream. On the one hand, any hydrogen halide that exits in the overhead stream is recycled to the regeneration zone where it is useful in maintaining the halide content of the catalyst that exits the regeneration zone. On the other hand, any hydrogen halide that exits in the bottom stream and is then recovered in the alkylate fractionation zone overhead stream is recycled to the alkylation reaction zone. It is believed that reintroduction of hydrogen halide to the alkylation reaction zone has a different effect on the production of alkylate than the reintroduction of molecular hydrogen to the alkylation reaction zone. Even though some of the olefinic alkylating agent may react with reintroduced hydrogen halide and thereby form a halogenated paraffin, it is thought that that halogenated paraffin may nevertheless react with the alkylation substrate to produce alkylate. By contrast, any olefinic alkylating agent that reacts with molecular hydrogen is believed to form a paraffin that is unhalogenated and which will not readily react with the alkylation substrate to produce alkylate.

Nevertheless, the hydrogen fractionation zone is generally operated to achieve a desired split between the hydrogen halide which exits in the overhead stream and the hydrogen halide which exits in the bottom stream, in order to optimize the hydrogen halide that is present in the regeneration zone on the one hand and in the reaction zone on the other hand. Generally from about 30 to about 60%, and preferably from about 40 to about 50%, of the moles of hydrogen halide that enter the hydrogen fractionation zone exit in the overhead stream, and therefore generally from about 40 to about 70%, and preferably from about 50 to about 60%, of the entering moles of hydrogen halide exit in the bottom stream. The overhead stream of the hydrogen fractionation zone contains generally from about 0.1 to about 10 mol-% hydrogen halide, and preferably from about 0.5 to about 5 mol-% hydrogen halide. The bottom stream of the hydrogen fractionation zone contains generally from about 0.01 to about 1 mol-% hydrogen halide, and preferably from about 0.05 to about 0.5 mol-% hydrogen halide. Compared to the liquid-phase stream produced by a vapor-liquid separator, this invention's hydrogen fractionation zone produces a bottom stream that has a lower concentration of molecular hydrogen, given the same split of the entering hydrogen chloride between, on the one hand, the vapor-phase and liquid-phase streams of the vapor-liquid separator and, on the other hand, the overhead and bottom streams of the hydrogen fractionation zone.

Within this invention's broadest scope, the alkylation process of this invention has at least one regeneration zone and the effluent from at least one of the regeneration zones passes to at least one hydrogen fractionation zone. However, if there is more than one regeneration zone, there may be a separate hydrogen fractionation zone for each regeneration effluent, or there may be one or more common hydrogen fractionation zones that are fed more than one regeneration effluent. In order to minimize the capital cost of building hydrogen fractionation zones where there is more than one regeneration zone, however, it is preferred that the effluents from all of the regeneration zones pass to a single, common hydrogen fractionation zone.

The alkylation reaction effluent passes to the alkylate fractionation zone. In addition, the bottom stream of the hydrogen fractionation zone also passes to the alkylate fractionation zone. The alkylate fractionation zone removes the alkylation substrate and halogen-containing species from the alkylate, so that they can be recycled to the alkylation reaction zone.

Although the alkylate fractionation zone may be a fractionation column that has either a rectification section without a stripping section or a stripping section without a rectification section, preferably the alkylate fractionation zone comprises a fractionation column having both rectification and stripping sections. The rectification section of the alkylate fractionation zone contains generally from 1 to 20 trays, preferably from 3 to 10 trays, and more preferably from 1 to 5 trays, presuming as above that the trays have an efficiency of about 60%. The stripping section of the alkylate fractionation zone contains generally from 1 to 150, preferably from 30 to 100, and more preferably from 50 to 75 trays, based on the assumption that these trays in the stripping section have an efficiency of from about 75 to about 100%. The alkylate fractionation column, its trays, and its other internals may be constructed from carbon steel.

The operating conditions of the alkylate fractionation column include a bottoms temperature of generally from about 325° F. to about 425° F. (163 to 218° C.) and preferably from about 330° F. to about 380° F. (166 to 193° C.), an overhead temperature of generally from about 120° F. to about 160° F. (49 to 71° C.) and preferably from about 120° F. to about 150° F. (49 to 66° C.), and an overhead pressure of generally from about 120 psi(g) to about 200 psi(g) (827 to 1379 kPa(g)). The overhead stream of the alkylate fractionation column has a concentration of molecular hydrogen of generally less than about 500 mol-ppm hydrogen, and preferably less than about 100 mol-ppm hydrogen. The quantity of molecular hydrogen that is present in the overhead stream is such that, if all of the molecular hydrogen in the overhead stream ultimately passed to the alkylation reaction zone, then, even if all of that molecular hydrogen reacted with alkylating agent that is being charged to the alkylation reaction zone, then preferably less than 1%, and more preferably less than 0.5%, of the total alkylating agent charged to the alkylation reaction zone would be rendered ineffective to react with the alkylation substrate by such reaction. In another embodiment, the ratio of the moles of molecular hydrogen in the net overhead stream withdrawn from the alkylate fractionation column to the moles of monoolefinic alkylating agent passed to the alkylation reaction zone is generally less than 0.01, and preferably less than 0.005. In yet another embodiment, the moles of molecular hydrogen in the net alkylate fractionation column overhead stream is generally less than 1%, and preferably less than 0.5%, of the moles of carbon-carbon double bonds in the olefinic alkylating agent passed to the alkylation reaction zone.

Figure 2:
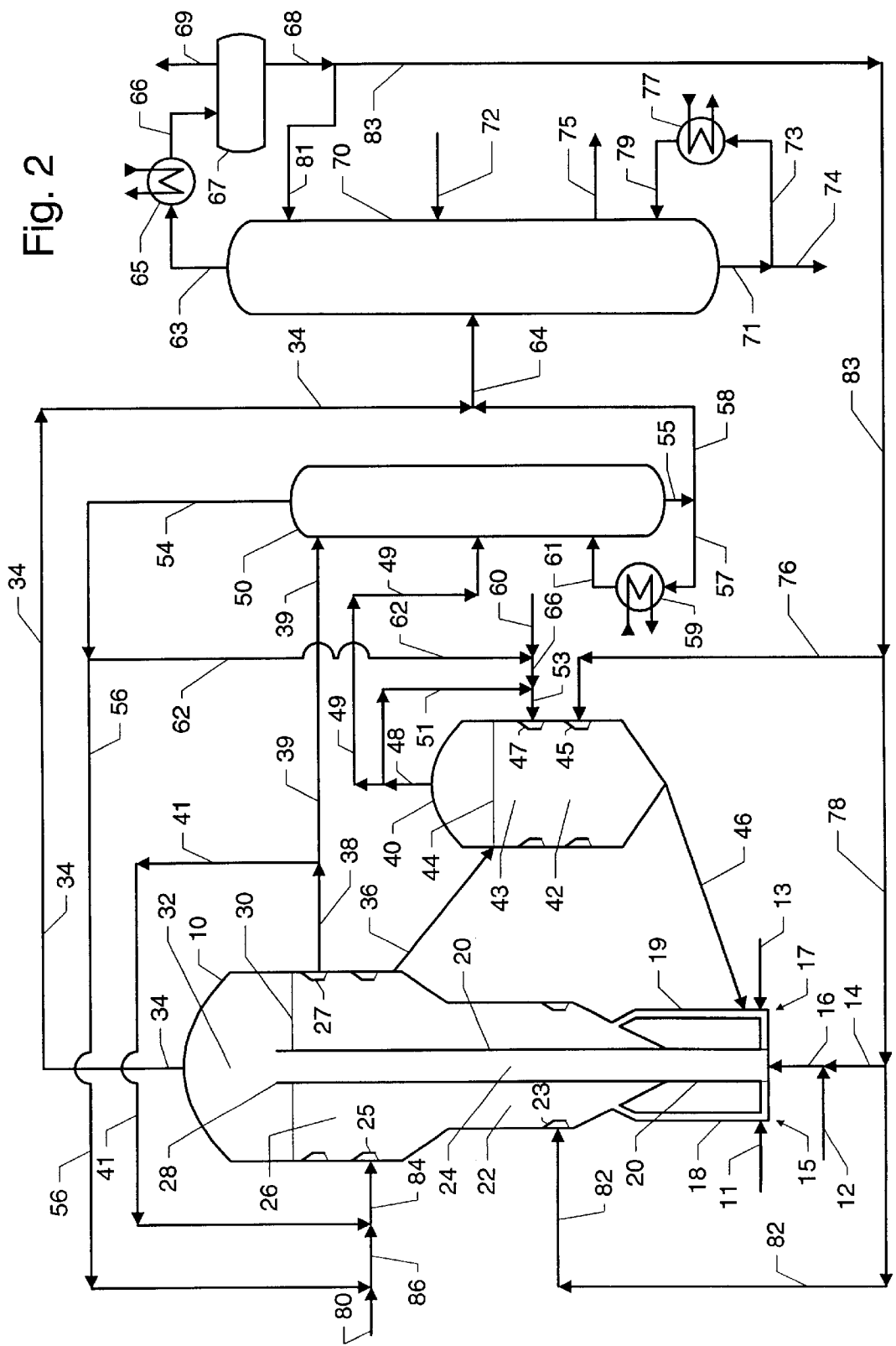

FIGS. 1 and 2 show embodiments of the process of the subject invention. For clarity and simplicity, some items associated with the operation of the embodiments have not been shown. These items include flow and pressure control valves, heaters, pumps, compressors, heat exchangers, temperature and pressure monitoring systems, vessel internals, etc., which may be of customary design. FIGS. 1 and 2 are not intended to limit the scope of the present invention as set forth in the claims. In addition, the description that follows is written in terms of isobutane as the alkylation substrate and a mixture of butene isomers as the alkylation agent, but the choice of these particular reactants for the following description is also not intended to limit the scope of the invention as set forth in the claims.

Referring now to FIG. 1, a liquid phase stream comprising isobutane flows through line 14, and a liquid phase stream comprising butene isomers enters the process through line 12. The isobutane combines with the butene isomers, and the combined stream moves through line 16 to the bottom of riser-reactor 20 in vessel 10. The injection of this liquid results in the upward flow of the contents of the riser-reactor 20 including solid catalyst which travels downward through multiple transfer lines, represented by lines 18 and 19, at rates controlled by L-valves 15 and 17, respectively. Liquid phase isobutane flows into L-valves 15 and 17 through lines 11 and 13, respectively, at rates sufficient to cause a continuous liquid and solid flow through transfer lines 18 and 19. Lines 18 and 19 will, therefore, deliver streams of catalyst to the bottom of riser-reactor 20. This catalyst is admixed with the entering combined reactant stream in line 16 and catalyzes the reaction of butenes with isobutane to form $C_8$ product hydrocarbons. The reaction products, the residual isobutane, and the now used catalyst exit from the top 28 of riser-reactor 20 and enter a large volume cylindrical separation chamber 32. The reaction of the olefins and the isobutane takes place in cylindrical space 24 defined by riser-reactor 20.

The low liquid velocities present within separation chamber 32 allow the liquids in the riser-reactor to separate from the solid particulate catalyst. The liquids that exit the riser-reactor 20 comprise alkylate, isobutane, and other hydrocarbons, and these are recovered in a reactor effluent that exits through line 34. The solid catalyst particles settle downward and form catalyst particle bed 26 having an upper limit or surface 30. Although the catalyst particles in bed 26 may be fluidized to any extent above the point of minimum fluidization, bed 26 is preferably a dense fluidized bed or a moving packed bed, and more preferably a moving packed bed. A liquid phase stream, which comprises isobutane, dissolved hydrogen, and materials present in the portion of the mild regeneration effluent that is recycled in line 41, passes into vessel 10 through line 84. A conventional fluid flow distributor, such as annular baffle 25, is used at or near the point of introduction of the fluid in line 84 into vessel 10 in order to uniformly distribute the fluid through bed 26. Annular baffles are disclosed in U.S. Pat. Nos. 4,662,081 (Greenwood); 4,665,632 (Greenwood); and 5,397,458 (Micklich et al.). Other suitable conventional fluid flow distributors include pipe distributors and conical baffles. By being contacted with hydrogen-saturated isobutane, the catalyst within bed 26 is subjected to a mild regeneration procedure, which removes heavy compounds from the catalyst.

The fluid entering vessel 10 through line 84 together with isobutane entering through line 82 gradually travel upward through bed 26 in vessel 10 and is withdrawn through line 38. The elevation of the point of withdrawal of line 38 is higher in bed 26 than the point of introduction of the liquid fluid in line 84, meaning that the point of withdrawal of line 38 is between the point of introduction of line 84 and the upper limit or surface 30 of bed 26. In order to effect withdrawal of up-flowing fluids from the down-flowing catalyst particles, conventional fluid flow collectors, such as annular baffle 27, and particle distributors may be used. Other suitable conventional fluid collectors include pipe collectors, and conventional particle distributors include conical baffles and disengagers which provide a low velocity disengaging space to allow liquids to be drawn upward while permitting solid particulate catalyst to settle downward. The thus collected liquid phase hydrocarbons along with any entrained hydrogen, as well as heavy compounds, are removed from vessel 10 through line 38 as a mild regeneration effluent. Although the mild regeneration effluent may be passed in its entirety through lines 39 and 52 to hydrogen stripper 50, the mild regeneration effluent is preferably divided into two portions. Each portion is preferably, but is not necessarily, an aliquot portion of the mild regeneration effluent. As used herein, the term "aliquot portion" of a stream means a portion of the stream that has essentially the same composition as the stream. Thus, in FIG. 1, an aliquot portion of the mild regeneration effluent is recycled through line 41, combines with the stream flowing in line 86, and re-enters bed 26 via line 84 and annular baffle 25.

The major portion of the used catalyst retained in catalyst particle bed 26 passes downward through vessel 10 to catalyst particle bed 22. In bed 22, the catalyst flows downward countercurrent to up-flowing isobutane, which has a concentration of molecular hydrogen of less than 500 mol-ppm hydrogen and which is charged to vessel 10 through line 82. The purpose of this contacting or washing of the catalyst with isobutane having a concentration of molecular hydrogen of less than 500 mol-ppm hydrogen is to prevent or at least minimize the entrance of molecular hydrogen into transfer lines 18 and 19 and ultimately into riser-reactor 20, where the molecular hydrogen could saturate olefins added by line 12. If the catalyst employed in the process does not promote the hydrogenation of the olefins, then this washing procedure may be eliminated. Catalyst particle bed 22 may be fluidized to any extent above the point of minimum fluidization or may be a dense fluidized bed, but preferably bed 22 is a moving packed bed. The isobutane liquid having a concentration of molecular hydrogen of less than 500 mol-ppm hydrogen that enters vessel 10 through line 82 is distributed uniformly across bed 22 by an annular baffle 23. The isobutane along with the purged molecular hydrogen which exits the top of bed 22 will gradually travel upward through vessel 10 as previously mentioned, flowing through bed 26 and being collected via annular baffle 27, and withdrawn from vessel 10 through line 38.

A second and smaller portion of the catalyst present in the catalyst particle bed 26 is withdrawn through line 36. This smaller stream of catalyst comprises both solid catalyst particles and liquid phase hydrocarbons and is passed to an external regenerator 40. The elevation of the point of addition of line 36 to external regenerator 40 is the same as or higher than the upper limit or surface 44 of bed 42. The catalyst is retained in external regenerator 40 for some average time set by the transfer rate of catalyst in line 36 and the volume of catalyst in external regenerator 40. This second catalyst stream may have a uniform flow rate over time, but a variable flow rate could also be used to facilitate batch regeneration.

Within external regenerator 40, the solid particulate catalyst forms catalyst particle bed 43 having an upper limit or surface 44. Although the catalyst particles in bed 43 may be fluidized to any extent above the point of minimum fluidization, bed 43 may be a dense fluidized bed or a moving packed bed. A liquid phase stream, which comprises isobutane, dissolved hydrogen, and materials present in the portion of the severe regeneration effluent that is recycled in line 51, passes into external regenerator 40 through line 53.

Annular baffle 47 is used at or near the point of the introduction of the fluid in line 53 into external regenerator 40 in order to uniformly distribute the fluid through bed 43. The stream in line 53, which is at a higher temperature than the stream in line 84, is heated by means not shown to a temperature to cause a more intense regeneration and a higher temperature in bed 43 than bed 26. The temperature in bed 43 is, however, insufficient to vaporize the liquid phase hydrocarbons that enter external regenerator 40 through lines 53, and bed 43 operates in the liquid phase.

The fluid entering external regenerator 40 through line 53 together with isobutane entering through line 76 gradually move upward through bed 43, exit bed 43 through upper limit or surface 44, and is withdrawn through line 48. Usually, the elevation of the point of withdrawal of line 48 is not only above the upper limit or surface 44 of bed 43 but also at or near the highest point in external regenerator 40. The liquid phase hydrocarbons along with any entrained hydrogen, as well as heavy compounds which have been removed from the catalyst that has undergone severe regeneration reach the top of external regenerator 40 and are removed through line 48 as the severe regeneration effluent. Although the severe regeneration effluent may be passed in its entirety through lines 49 and 52 to hydrogen stripper 50, the severe regeneration effluent is preferably divided into two portions. Each portion is preferably, but is not necessarily, an aliquot portion of the mild regeneration effluent. Thus, an aliquot portion of the severe regeneration effluent is recycled through line 51, combines with the stream flowing in line 66, and re-enters bed 43 via line 53 and annular baffle 47.

The severely regenerated catalyst retained in catalyst particle bed 43 passes downward through external regenerator 40 to catalyst particle bed 42. In bed 42, the catalyst flows downward countercurrent to isobutane having a concentration of molecular hydrogen of less than 500 mol-ppm hydrogen, which is charged to external regenerator 40 through line 76. The purpose of this contacting or washing of the catalyst with isobutane having a concentration of molecular hydrogen of less than 500 mol-ppm hydrogen is to prevent or at least minimize the entrance of molecular hydrogen into line 46 and ultimately into riser-reactor 20, where the molecular hydrogen could saturate olefins. If the catalyst employed in the process does not promote the hydrogenation of the olefins, then this washing may be eliminated. Bed 42 may be fluidized to any extent above the point of minimum fluidization, may be a dense fluidized bed, or may be a moving packed bed. The temperature in bed 42 is insufficient to vaporize the isobutane that enters external regenerator 40 through lines 76, and bed 42 operates in the liquid phase. The entering isobutane liquid having a concentration of molecular hydrogen of less than 500 mol-ppm hydrogen is distributed uniformly across bed 42 by an annular baffle 45. The isobutane and the purged hydrogen, which exit the top of bed 42, gradually travel upward through external regenerator 40 by flowing through bed 43 and are ultimately withdrawn from external regenerator 40 through line 48.

In the case of batch operation of external regenerator 40, bed 42 may be a fixed or packed bed during severe regeneration, and bed 43 may be a fixed or packed bed during washing with the isobutane having a concentration of molecular hydrogen of less than 500 mol-ppm hydrogen.

A stream of severely regenerated catalyst is removed from external regenerator 40 via line 46. This rate is preferably approximately equal to the rate at which catalyst is fed into external regenerator 40 but may fluctuate over short periods.

The highly or severely regenerated catalyst may be cooled to a temperature below about 100° F. (38° C.) by a catalyst cooler located below bed 42 in external regenerator 40 or at a point along line 46. The severely regenerated catalyst in line 46 commingles with catalyst that has been mildly regenerated flowing through transfer line 19. The stream of liquid-phase isobutane from line 13 causes the commingled catalyst to flow through L-valve 17 and through transfer line 19 to the bottom of riser-reactor 20.

The circulation of the catalyst through external regenerator 40 may require the catalyst to be heated and cooled. The utility requirements of the process also require that the heat of reaction of the alkylation reaction be removed. These activities can be integrated with the operation of the products recovery section of the process. For instance, the heat available in the catalyst that has been severely regenerated and is being returned to riser-reactor 20 can be removed by a cooler and supplied to the product recovery section. Alternatively, the heated coolant from such a cooler may be passed to external regenerator 40 in order to provide heat to the catalyst undergoing severe regeneration.

An aliquot portion of the severe regeneration effluent in line 49 combines with an aliquot portion of the mild regeneration effluent in line 39, and the combined stream flows through line 52 to hydrogen stripper 50. The hydrogen stripper 50 typically contains a vapor-liquid contacting medium such as trays or packing, and the combined stream usually enters hydrogen stripper 50 at an elevation above the upper limit or surface of the contacting medium.

The hydrogen stripper 50 strips molecular hydrogen from liquid isobutane and liquid heavy compounds as these liquids descend through hydrogen stripper 50. Hydrogen chloride, which is less volatile than molecular hydrogen at the operating conditions of hydrogen stripper 50, is also stripped from the descending liquids. The molecular hydrogen and hydrogen chloride are withdrawn from hydrogen stripper 50 in an stripper overhead stream via line 54. The stripper overhead stream is a vapor or gaseous stream that comprises molecular hydrogen, hydrogen chloride, and isobutane, but has low concentrations of alkylate and heavy compounds.

The stripper overhead stream can be recycled to bed 26, bed 43, or as shown in FIG. 1 both beds 26 and 43. An aliquot portion of the stripper overhead stream in line 54 passes through line 56 and combines with makeup molecular hydrogen entering the process via line 80 to form a combined stream in line 86. The combined stream in line 86 in turn combines with the recycled portion of the mild regeneration effluent in line 41 and thereby forms the stream in line 84 which enters bed 26. Similarly, another aliquot portion of the stripper overhead stream in line 54 passes through line 62, combines with makeup molecular hydrogen entering the process via line 60, thereby forming a combined stream in line 66. That combined stream in turn mixes with a recycled portion of the severe regeneration effluent in line 51 and thereby forms the stream in line 53 which enters bed 43. Although this description specifically describes the portions of the stripper overhead stream that pass to beds 26 and 43 as aliquot portions, any other portion of the stripper overhead stream may also be passed to beds 26 and/or 43. Any portion of the stripper overhead stream may be cooled or heated, or condensed or vaporized, prior to being passed to either bed 26 or 43.

A bottom stream exits hydrogen stripper 50 through line 55. The hydrogen stripper bottom stream is liquid phase and comprises isobutane and hydrocarbons that are heavier than isobutane, including pentanes, alkylate, and heavy compounds. It is an essential part of this invention that hydrogen stripper 50 strips at least a portion of the molecular hydrogen from the descending liquids, so that the molecular hydrogen content of the hydrogen stripper bottom stream in line 55 is generally less than that of the combined stream entering the hydrogen stripper 50 via line 52. One portion of the stripper bottom stream passes through line 57 and reboiler 59, and returns through line 61 to hydrogen stripper 50. Reboiler 59 provides heat required for stripping molecular hydrogen from descending liquids in hydrogen stripper 50. If, however, the combined stream that flows through line 52 to hydrogen stripper 50 provides enough heat to effect the required separation, then reboiler 59 and lines 57 and 61 can be eliminated.

Another portion of the stripper bottom stream flows through line 58, combines with reactor effluent flowing through line 34, and the combined stream enters alkylate product recovery column 70. Thus, the combined stream in line 64 comprises alkylate, heavy compounds, isobutane, hydrogen chloride, and trace if any hydrogen. The primary purpose of alkylate product recovery column 70 is to separate isobutane from normal butane and heavier liquid hydrocarbons including the product alkylate, and therefore column 70 is commonly, and hereinafter, referred to as an "isostripper." Makeup field butanes, comprising isobutane and normal butane, enter isostripper 70 through line 72. Isostripper 70 is a trayed fractionation column with a stripping section and a rectification section. Typically, isostripper 70 has approximately 60 to 80 trays, based on the assumption that each tray has an efficiency of 60–90%. A sidecut stream comprising normal butane is withdrawn from a sidecut tray located between the feed tray and the bottom of isostripper 70 and exits the process through line 75. An overhead stream comprising isobutane and hydrogen chloride is withdrawn from the top of isostripper 70 and passes through line 63. Typically, most of the isostripper overhead stream is condensed in condenser 65 and then passes through line 66 to receiver 69, where a vapor-liquid phase separation occurs. An overhead vapor stream comprising hydrogen chloride, hydrocarbons lighter than isobutane, hydrogen, if any, and any other uncondensable components is withdrawn from receiver 67 through line 69. An overhead liquid stream comprising isobutane and having a concentration of molecular hydrogen of less than 500 mol-ppm hydrogen is withdrawn from line 68. The overhead liquid stream generally also comprises hydrogen chloride. An aliquot portion of the overhead liquid stream returns to the top of isostripper 70 as reflux, and the remaining aliquot portion flows through line 83. The aliquot portion flowing in line 83 is further divided into aliquot portions, thereby providing streams containing isobutane and hydrogen chloride and which has a concentration of molecular hydrogen of less than 500 mol-ppm hydrogen via line 53 to bed 42 in external regenerator 40; to the bottom of riser-reactor 20 via lines 78, 14, an 16; and to bed 22 in vessel 10 via lines 78 and 82.

An isostripper bottoms stream comprising alkylate is withdrawn from isostripper 70 through line 71. One portion of the isostripper bottom stream passes through line 73 and reboiler 77, and returns through line 79 to isostripper 70. Another portion of the isostripper bottoms stream forms the net product alkylate and is recovered from the process through line 74.

In a variation on the flow arrangement of FIG. 1 but not shown in FIG. 1, the stripper overhead stream in line 54 first passes to a condenser which condenses the isobutane. The condenser outlet stream, which is a mixture of molecular hydrogen, hydrogen chloride, and condensed isobutane, then passes to an overhead receiver, which separates the mixture into vapor and liquid phases. The vapor phase, comprising mostly molecular hydrogen and hydrogen chloride, recycles to beds 26 and/or 43, and the isobutane liquid phase may be passed to beds 26 and/or 42, to riser-reactor 20, or to another location in the process where a stream of liquid isobutane may be useful, such as reflux to the hydrogen stripper itself. This variation is useful when not only is it desired to recycle the stripped isobutane on the one hand separately and independently of the stripped molecular hydrogen and hydrogen chloride on the other hand but when also a very low molecular hydrogen content in the hydrogen stripper bottoms stream is desired. In this case, the hydrogen stripper is operated at severe stripping conditions, thereby stripping from the hydrogen stripper bottoms and into the hydrogen stripper overhead not only more molecular hydrogen but also more isobutane. Using a condenser/receiver system in the hydrogen stripper overhead thus allows the stripped isobutane to be separated from the stripped molecular hydrogen and hydrogen chloride.

FIG. 2 shows another embodiment of the invention wherein the catalyst in the severe regeneration zone in external regenerator 40 is contacted with a vapor phase regeneration stream rather than with a liquid phase regeneration stream as in FIG. 1. Items in FIG. 2 that correspond to items in FIG. 1 have the same reference number. In FIG. 2, heater(s) which are not shown vaporize the isobutane passing to external regenerator so that the stream that enters via lines 53 and 76 are vapor phase. The effluent of the severe regeneration zone is also vapor phase and leaves external regenerator 40 via line 48. The portion of the mild regeneration effluent in line 39 and the portion of the severe regeneration effluent in line 49 flow separately to hydrogen stripper 50, with the liquid phase mild regeneration effluent portion entering at a location in the upper portion of hydrogen stripper 50 and the vapor phase severe regeneration effluent portion entering at a lower location in hydrogen stripper 50. If hydrogen stripper 50 has n trays numbered from the top of the hydrogen stripper, then the feed point of the mild regeneration effluent portion is preferably at a location above the first tray and the feed point of the severe regeneration effluent portion is below tray n/2.

The beneficial operation of this invention will be further described in the context of an exemplified preferred embodiment which is the alkylation with a solid catalyst of isobutane with butene and pentene and the regeneration of the solid catalyst with isobutane containing dissolved hydrogen. The illustration of this invention in terms of a preferred embodiment is not meant to limit the claims of this invention to the particular details disclosed herein. The example presented herein is based on engineering calculations and actual laboratory experiments.

EXAMPLE

The flow scheme for this Example is essentially that of FIG. 1. An olefinic and a paraffinic feed having the compositions shown in Table 1 pass to an alkylation reaction zone employing a solid alkylation catalyst and producing a reaction effluent having the composition shown in Table 2. The solid alkylation catalyst is regenerated in a mild regeneration zone and in a severe regeneration zone, and effluents having the compositions shown in Table 2 are withdrawn from these two zones. The regeneration effluents are passed to a hydrogen stripper, which produces an overhead stream and a bottom stream having the compositions shown in Table 2. About 99 percent of the molecular hydrogen and from about 40 to about 60 percent of the hydrogen chloride that enters the hydrogen stripper with the regeneration effluents exits in the hydrogen stripper overhead stream, with the remainder of the entering molecular hydrogen and hydrogen chloride exiting with the hydrogen stripper bottom stream. The reactor effluent and the hydrogen stripper bottom stream are combined into a combined feed that has the composition shown in Table 2 and is fed to an isostripper. Because the combined feed to the isostripper is in part formed from the hydrogen stripper bottom stream, which contains only 0.02 mol-% hydrogen, rather than from the mild regeneration effluent (2.3 mol-% hydrogen) or the severe regeneration effluent (2.8 mol-% hydrogen), the combined feed to the isostripper contains a low concentration of molecular hydrogen (only 0.006 mol-%). Accordingly, the isostripper need not be designed or operated in a manner so that large quantities of molecular hydrogen must be separated from the entering hydrocarbons in order to prevent the molecular hydrogen from being recycled to the alkylation reaction zone.

TABLE 1

Composition of Feeds—mol %

| | Olefinic Feed | Paraffinic Feed |
|---|---|---|
| Molecular hydrogen | — | 0.027 |
| Hydrogen chloride | — | 0.2 |
| Methane | — | 0.2 |
| Ethane | — | 0.6 |
| Propane | 0.1 | 8.4 |
| Propene | 0.2 | — |
| Butanes | 34.4 | 89.7 |
| Butenes | 44.8 | — |
| Pentanes | 12.3 | 0.8 |
| Pentenes | 8.0 | — |
| Hexanes and heavier hydrocarbons | 0.2 | 0.1 |
| Total | 100.0 | 100.0 |

TABLE 2

Composition of Streams — mol %

| Stream | Reactor Effluent | Mild Regeneration Effluent | Severe Regeneration Effluent | Hydrogen Stripper Overhead | Hydrogen Stripper Bottom | Combined Feed to Isostripper |
|---|---|---|---|---|---|---|
| Line Number in FIG. 1 | 34 | 39 | 49 | 54 | 55 | 64 |
| Hydrogen | — | 2.3 | 2.8 | 34.7 | 0.020 | 0.006 |

TABLE 2-continued

| | Composition of Streams — mol % | | | | | |
|---|---|---|---|---|---|---|
| Stream | Reactor Effluent | Mild Regeneration Effluent | Severe Regeneration Effluent | Hydrogen Stripper Overhead | Hydrogen Stripper Bottom | Combined Feed to Isostripper |
| Hydrogen Chloride | 0.1 | 0.3 | 0.3 | 1.9 | 0.2 | 0.1 |
| Hydrocarbons | 99.9 | 97.4 | 96.9 | 63.4 | 99.8 | 99.9 |
| Total | 100.0 | 100.0 | 100.0 | 100.0 | 100.0 | 100.0 |

What is claimed is:

1. An alkylation process comprising:
   a) passing a first feed stream comprising a paraffinic alkylation substrate and a second feed stream comprising an olefinic alkylating agent to an alkylation reaction zone operated at alkylation conditions selected to react the paraffinic alkylation substrate and the olefinic alkylating agent in the presence of a solid catalyst to produce alkylate, the alkylation conditions being sufficient to deposit heavy compounds on the solid catalyst in the alkylation reaction zone, and withdrawing from the alkylation reaction zone an alkylation reaction effluent comprising the alkylate and the paraffinic alkylation substrate;
   b) withdrawing a first catalyst stream comprising solid catalyst having heavy compounds deposited thereon from the alkylation reaction zone, passing at least a portion of the first catalyst stream to a first regeneration zone, contacting the solid catalyst having heavy compounds deposited thereon with molecular hydrogen in the first regeneration zone at first regeneration conditions selected to remove at least a portion of the heavy compounds from the solid catalyst having heavy compounds deposited thereon and to at least partially regenerate the solid catalyst having heavy compounds deposited thereon;
   c) withdrawing a second catalyst stream comprising at least partially regenerated solid catalyst from the first regeneration zone, and passing at least a portion of the second catalyst stream to the alkylation reaction zone;
   d) withdrawing a first regeneration effluent comprising molecular hydrogen and the heavy compounds from the first regeneration zone, passing at least a portion of the first regeneration effluent to a hydrogen fractionation zone, and recovering from the hydrogen fractionation zone a hydrogen-enriched stream having a first concentration of molecular hydrogen and a hydrogen-depleted stream comprising the heavy compounds and having a second concentration of molecular hydrogen that is less than the first concentration of molecular hydrogen;
   e) passing at least a portion of the hydrogen-enriched stream to the first regeneration zone;
   f) passing at least a portion of the alkylation reaction effluent and at least a portion of the hydrogen-depleted stream to an alkylate fractionation zone, and withdrawing from the alkylate fractionation zone a recycle stream comprising the paraffinic alkylation substrate;
   g) forming the first feed stream from at least a portion of the recycle stream; and
   h) recovering the alkylate from the alkylate fractionation zone.

2. The process of claim 1 further characterized in that the solid catalyst comprises a halide, the alkylation reaction effluent comprises a halogen-containing species, and the recycle stream comprises the halogen-containing species.

3. The process of claim 1 further characterized in that the first regeneration effluent has a concentration of molecular hydrogen of greater than about 0.5 mol-% hydrogen.

4. The process of claim 1 further characterized in that the ratio of the moles of molecular hydrogen in the first feed stream to the moles of olefinic alkylating agent in the second feed stream is less than 0.01.

5. The process of claim 1 further characterized in that the moles of molecular hydrogen in the first feed stream is less than 1% of the moles of carbon-carbon double bonds in the olefinic alkylating agent in the second feed stream.

6. The process of claim 1 further characterized in that the first feed stream comprises molecular hydrogen, and molecular hydrogen and the olefinic alkylating agent react in the alkylation reaction zone to form a resultant compound, wherein less than 1% of the olefinic alkylating agent passed to the alkylation reaction zone reacts with molecular hydrogen to form the resultant compound, and wherein the resultant compound is ineffective to react with the paraffinic alkylation substrate at the alkylation conditions.

7. The process of claim 1 further characterized in that the hydrogen-depleted stream has a concentration of molecular hydrogen of less than 1.0 mol-%.

8. The process of claim 1 further characterized in that the recycle stream has a concentration of molecular hydrogen of less than 500 mol-ppm hydrogen.

9. The process of claim 1 further characterized in that the solid catalyst comprises a halide, the first regeneration effluent comprises a halogen-containing species, and that from about 30 to about 60% of the halogen-containing species in the at least a portion of the first regeneration effluent is recovered from the hydrogen fractionation zone in the hydrogen-enriched stream.

10. The process of claim 1 further characterized in that the hydrogen-enriched stream comprises the paraffinic alkylation substrate.

11. The process of claim 1 further characterized in that the first regeneration conditions comprise at least a partial liquid phase.

12. The process of claim 2 wherein the halide is fluoride, chloride, or bromide.

13. The process of claim 2 wherein the halogen-containing species is selected from the group consisting of hydrogen fluoride, hydrogen chloride, and hydrogen bromide.

14. The process of claim 1 wherein the paraffinic alkylation substrate comprises a paraffin selected from the group consisting of 2-methylpropane, 2-methylbutane, 2,3-dimethylbutane, 2-methylpentane, and 3-methylpentane.

15. The process of claim 1 wherein the olefinic alkylating agent comprises an olefin selected from the group consisting of ethylene, propylene, 1-butene, cis-2-butene, trans-2-butene, and iso-butene.

16. The process of claim 1 further characterized in that a third catalyst stream comprising the solid catalyst having heavy compounds deposited thereon is withdrawn from the alkylation reaction zone, at least a portion of the third catalyst stream passes to a second regeneration zone, molecular hydrogen contacts the solid catalyst having heavy compounds deposited thereon in the second regeneration zone at second regeneration conditions to remove at least a portion of the heavy compound deposits from the solid catalyst having heavy compounds deposited thereon and to at least partially regenerate the solid catalyst having heavy compounds deposited thereon, a fourth catalyst stream comprising at least partially regenerated solid catalyst is withdrawn from the second regeneration zone, at least a portion of the fourth catalyst stream passes to the alkylation reaction zone, a second regeneration effluent comprising molecular hydrogen and heavy compounds is withdrawn from the second regeneration zone, and at least a portion of the second regeneration effluent passes to the hydrogen fractionation zone.

17. The process of claim 16 further characterized in that the first regeneration conditions comprise a first regeneration temperature and the second regeneration conditions comprise a second regeneration temperature that is greater than the first regeneration temperature.

18. The process of claim 1 further characterized in that a third catalyst stream comprising the solid catalyst having heavy compounds deposited thereon is withdrawn from the first regeneration zone, the third catalyst stream passes to a second regeneration zone, molecular hydrogen contacts the solid catalyst having heavy compounds deposited thereon in the second regeneration zone at second regeneration conditions to remove at least a portion of the heavy compound deposits from the solid catalyst having heavy compounds deposited thereon and to at least partially regenerate the solid catalyst having heavy compounds deposited thereon, a fourth catalyst stream comprising at least partially regenerated solid catalyst is withdrawn from the second regeneration zone, at least a portion of the fourth catalyst stream passes to the alkylation reaction zone, a second regeneration effluent comprising molecular hydrogen and heavy compounds is withdrawn from the second regeneration zone, and at least a portion of the second regeneration effluent passes to the hydrogen fractionation zone.

19. The process of claim 1 further characterized in that the hydrogen fractionation zone comprises a stripping zone.

20. The process of claim 1 further characterized in that the first regeneration effluent is divided into a first aliquot portion and a second aliquot portion, the first aliquot portion of the first regeneration effluent passes to the hydrogen fractionation zone, and the second aliquot portion of the first regeneration effluent is recycled to the first regeneration zone.

* * * * *